United States Patent [19]

Miyazawa et al.

[11] Patent Number: 4,904,409
[45] Date of Patent: Feb. 27, 1990

[54] OPTICALLY ACTIVE-1-(2-HALOGEN-SUBSTITUTED-PHENYL)-ETHANOL AND ITS DERIVATIVE

[75] Inventors: Kazutoshi Miyazawa; Ohno Kouji; Naoyuki Yoshida; Masakazu Kaneoya, all of Ichiharashi, Japan

[73] Assignee: Chisso Corporation, Osaka, Japan

[21] Appl. No.: 239,277

[22] Filed: Sep. 1, 1988

[30] Foreign Application Priority Data

Oct. 9, 1987 [JP] Japan .................... 62/255326
Oct. 9, 1987 [JP] Japan .................... 62/255325

[51] Int. Cl.$^4$ .............. G02F 1/13; C07C 69/76; C07D 239/02; C07D 211/72

[52] U.S. Cl. .............. 252/299.61; 252/299.01; 252/299.6; 252/299.63; 252/299.66; 350/350 R; 350/350 S; 544/298; 544/315; 544/316; 544/318; 544/334; 544/335; 546/286; 546/288; 546/301; 546/302; 546/342; 558/416; 558/426; 558/427; 560/55; 560/59; 560/61; 560/102; 560/106; 560/107

[58] Field of Search ........... 252/299.01, 299.5, 299.61, 252/299.63, 299.66, 299.6; 350/350 R, 350 S; 544/298, 315, 316, 318, 334, 335; 546/286, 288, 301, 302, 342; 558/416, 426, 427; 560/55, 59, 61, 102, 106, 107

[56] References Cited

U.S. PATENT DOCUMENTS

| | | |
|---|---|---|
| 4,725,688 | 2/1988 | Taguchi et al. ............. 252/299.61 |
| 4,728,458 | 3/1988 | Higuchi et al. ............. 252/299.65 |
| 4,737,313 | 4/1988 | Saito et al. ............... 252/299.63 |
| 4,764,619 | 8/1988 | Gunjima et al. ............ 252/299.63 |
| 4,765,924 | 8/1988 | Inoue et al. .............. 252/299.61 |
| 4,775,220 | 10/1988 | Yoshinaga et al. .......... 252/299.01 |

FOREIGN PATENT DOCUMENTS

| | | |
|---|---|---|
| 3515373 | 11/1986 | Fed. Rep. of Germany ......... 252/299.61 |
| 3534778 | 4/1987 | Fed. Rep. of Germany ......... 252/299.61 |
| 3600052 | 7/1987 | Fed. Rep. of Germany ......... 252/299.61 |
| 60-255779 | 12/1985 | Japan ....................... 252/299.61 |
| 61-174294 | 8/1986 | Japan ....................... 252/299.63 |
| 2181429 | 4/1987 | United Kingdom ............. 252/299.66 |
| 86/07055 | 12/1986 | World Int. Prop. O. ....... 252/299.61 |
| 87/05012 | 8/1987 | World Int. Prop. O. ....... 252/299.61 |
| 87/05316 | 9/1987 | World Int. Prop. O. ....... 252/299.61 |

*Primary Examiner*—Teddy S. Gron
*Attorney, Agent, or Firm*—Fred Philpitt

[57] ABSTRACT

An optically active compound having characteristics necessary for realizing liquid crystal compositions provided with suitable characteristics, particularly a negative temperature characteristic and a very high twistability, and a liquid crystal composition containing the compound are provided, which optically active compound is expressed by the formula

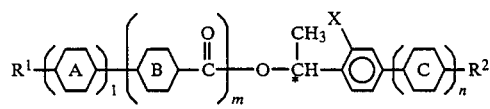

wherein $R^1$ and $R^2$ are 1–20 C alkyl or alkoxy or H; l, m and n are 0 or 1; X is F, Cl, Br or CN; and

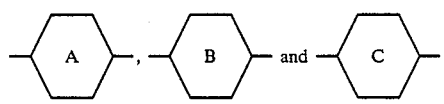

each independently represent

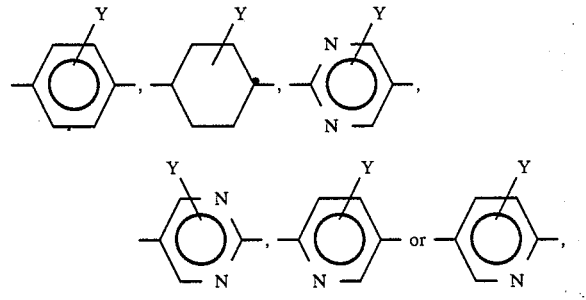

wherein Y is H, halogen or CN.

2 Claims, 2 Drawing Sheets

OPTICALLY ACTIVE-1-(2-HALOGEN-SUBSTITUTED-PHENYL)-ETHANOL AND ITS DERIVATIVE

BACKGROUND OF THE INVENTION

1. Field of the Invention

This invention relates to a novel organic compound and a liquid crystal composition containing the same. More particularly it relates to an organic compound having an optically active group and a liquid crystal composition containing the same.

2. Description of the Related Art

As to liquid crystal display elements, their use applications have been rapidly broadened due to improvements in circuit, driving mode and cell production technique and particularly due to improvement in characteristics of liquid crystal compositions filled in the elements. However, liquid crystal display elements still have a number of drawbacks to be overcome such as narrow angle of view, inferior contrast, low response rate, still small display capacity, reduction in the display quality due to ambient temperature change, etc. Among these, the reduction in the display quality due to ambient temperature change is originated from the temperature change in the threshold voltage Vth.

As a means usually employed in recent years, there is a method of adding a slight quantity of an optically active substance to a liquid crystal composition to suppress the reverse twist of liquid crystal molecules and thereby afford a right-turn or left-turn helical structure to the liquid crystal molecules so that a display quality is retained. For example, the method can have an advantageous effect upon the cases of TN (Twisted nematic) mode display element, recently proposed SBE (supertwisted birefringence effect) mode display element, etc.

However, if the twistability of an optically active substance added as a dopant is too low, it is necessary to add the dopant in a relatively high concentration in order to obtain a required pitch; hence this apparently has a disadvantageous effect upon other parameters of the liquid crystal composition. Thus, an optically active substance has been awaited, which has a high twistability i.e. a capability of exhibiting a shorter pitch when the substance is added in the same quantity to liquid crystals.

For example, when CB-15 (tradename of product made by BDH Company) or compounds recently disclosed in Japanese patent application laid-open Nos. Sho 62-81354/1987 and Sho 62-81355/1987 are added only in 1% by weight to nematic liquid crystal compositions, these compounds have a capability of exhibiting a pitch of about 10 μm; hence they can be regarded as practically usable optically active substances.

However, general known optically active substances including the above-mentioned compounds increase the pitch of liquid crystal substances with rise of temperature by the addition thereof; thus they often have an undesirable effect upon the pitch. For example, in the case of SBE mode, the intrinsic pitch P of liquid crystal compositions varies with temperature change, whereby the ratio of the intrinsic pitch (P) of the liquid crystal compositions to the cell thickness (d) of the display element (P/d) varies accordingly. The P/d value is usually 2 or less, but when it exceeds 2 due to the temperature change, the 270° twist changes to the 90° twist.

Further, in the aspect of improvement for enhancing the display capacity, it is necessary to improve the steepness of change in the transmittance in the case where a voltage is going to be impressed to a display element. G. Bauer and W. Fehlenback reported a calculation result that the steepness was notably improved by making the twist 270°, in the 15th Freiburg liquid crystal sympodium (1985), and in this case, too, it is necessary to be free from change in the intrinsic pitch due to temperature.

As a means for solving this problem, an optically active compound having negative temperature characteristics i.e. a substance for reducing its intrinsic pitch with temperature rise has recently been found and by blending a suitable quantity of this compound with an optically active substance having positive temperature characteristics, a composition having its intrinsic pitch unchanged due to temperature has been obtained (Emoto et al., Japanese patent application No. Sho 61-179194/1986).

However, any of currently reported substances having negative temperature characteristics have a low twistability; hence it is necessary to add such substances in a considerably high concentration in order to obtain a required pitch so that it is considered that they have various bad influences. Thus, in order to solve these problems, a substance having a short pitch and yet negative temperature characteristics has been desired.

The present inventors have made extensive research in order to develop an optically active compound having characteristics required for realizing a liquid crystal composition having suitable characteristics i.e. a negative temperature characteristic and a high twistability, and as result have achieved the present invention.

SUMMARY OF THE INVENTION

The object of the present invention is to provide an optically active compound having characteristics necessary for realizing liquid crystal compositions provided with suitable characteristics, particularly a negative temperature characteristic and a very high twistability.

The present invention resides in an optically active compound expressed by the formula

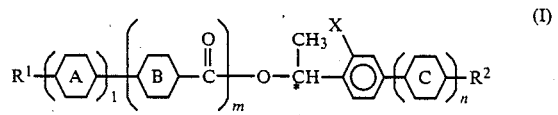

wherein $R^1$ and $R^2$ each represent an alkyl group or an alkoxy group each of 1 to 20 carbon atoms or hydrogen atom; l, m and n each represent 0 or 1; X represents fluorine atom, chlorine atom, bromine atom or cyano group; and

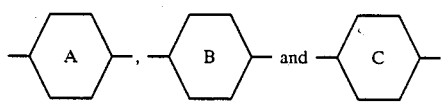

each independently represent

The compound of the formula (I) may be suitably prepared for example through the following route:
(a) Case of X=F, Cl or Br:

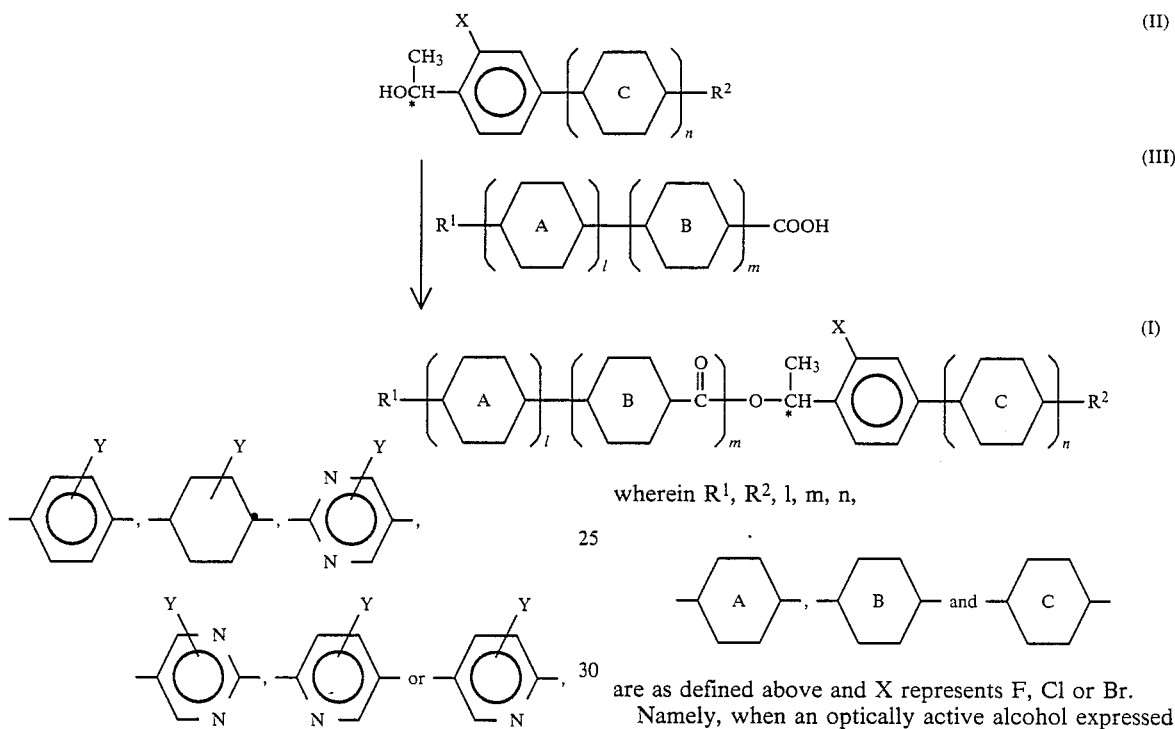

wherein $R^1$, $R^2$, l, m, n,

-A-, -B- and -C- are as defined above and X represents F, Cl or Br.

Namely, when an optically active alcohol expressed by the formula (II) is reacted with various carboxylic acids expressed by the formula (III), the compound of the formula (I) can be obtained.

(b) Case of converting X=Br to X=CN:

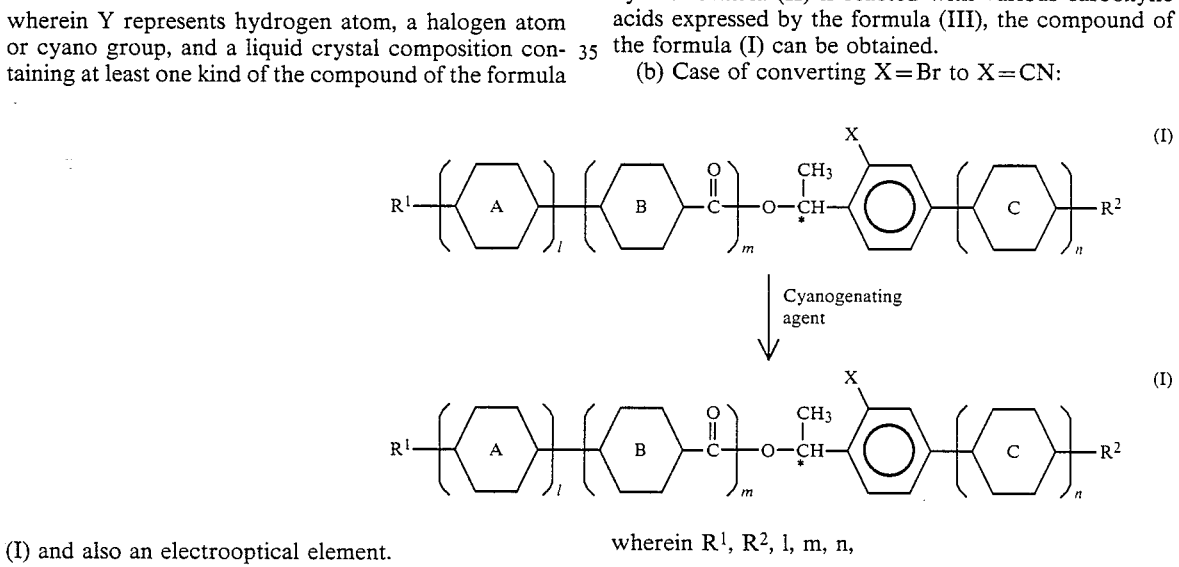

wherein $R^1$, $R^2$, l, m, n,

-A-, -B- and -C- are as defined above.

Namely, when the compound of X=Br obtained in the above (a) is cyanogenated, a compound of X=CN in the formula (I) is obtained.

Further, the compound of the above formula (II) (a compound of the formula (I) wherein l=m=0 and $R^1$=H) is obtained by optical resolution of a commercially available racemic alcohol or a racemic alcohol wherein Y represents hydrogen atom, a halogen atom or cyano group, and a liquid crystal composition containing at least one kind of the compound of the formula (I) and also an electrooptical element.

The present invention further resides in an optically active compound expressed by the formula (II) described below.

DETAILED DESCRIPTION OF PREFERRED EMBODIMENTS

Figure 1:
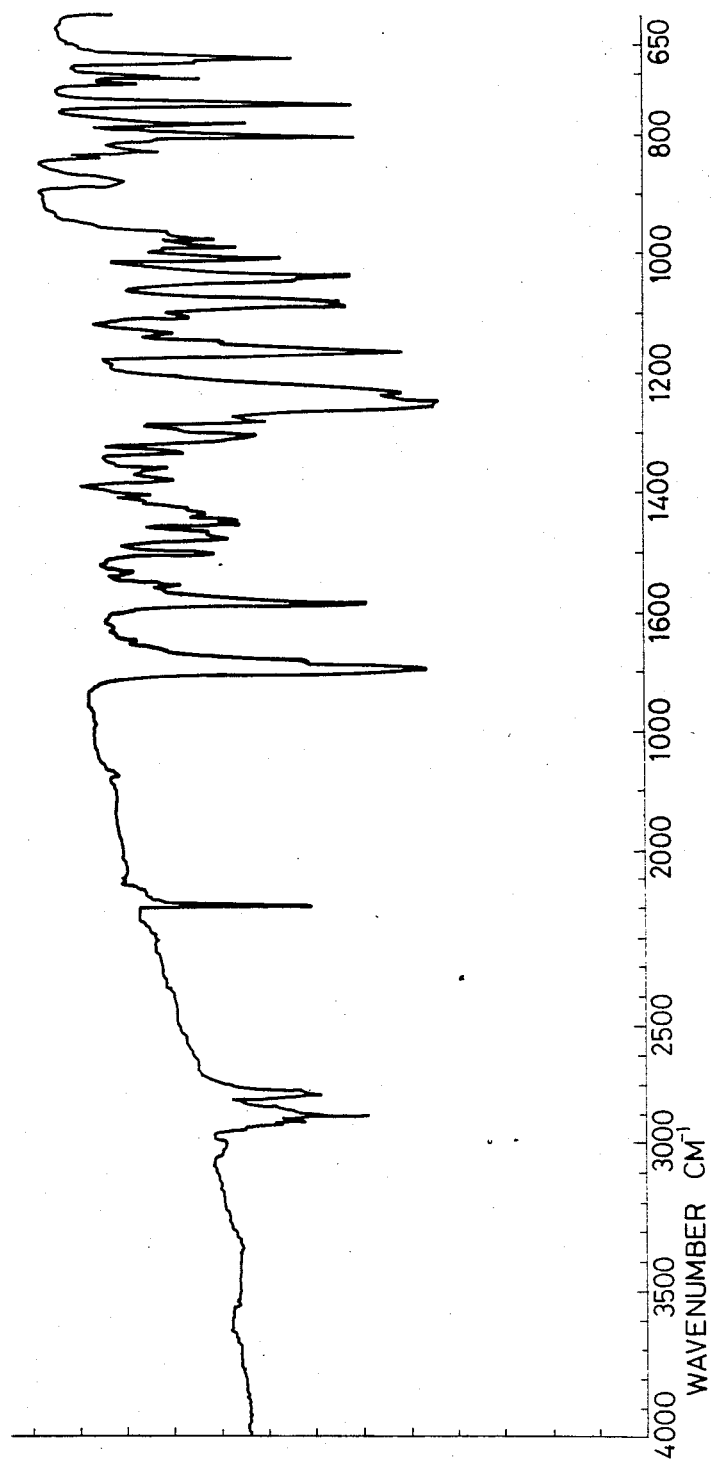
FIG. 1 shows an infrared absorption spectra chart of a compound obtained in Example 3 of the present invention.
Figure 2:
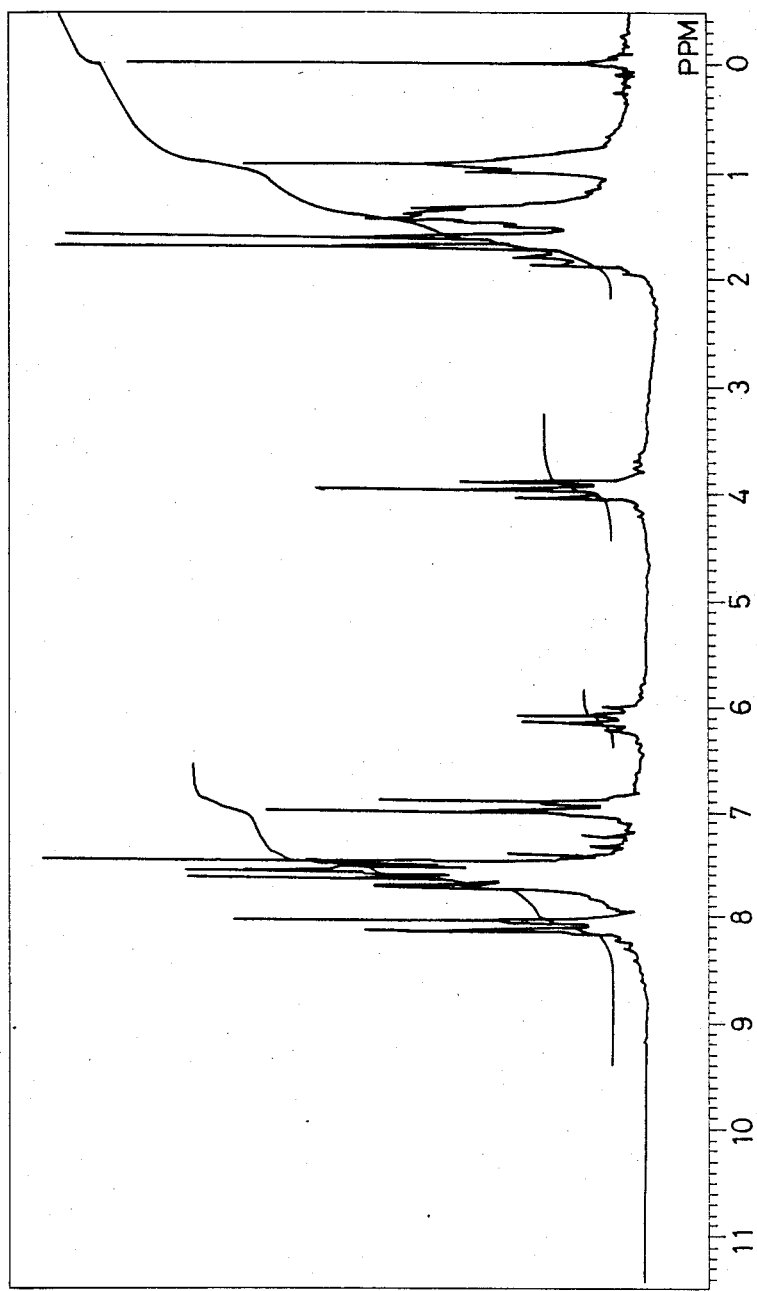
FIG. 2 shows an NMR chart of the compound.

Preparation of the compound of the formula (I) of the present invention will be described below.

prepared for example according to the following equation, through biochemical asymmetric ester exchange, asymmetric ester synthesis or asymmetric ester hydrolysis:

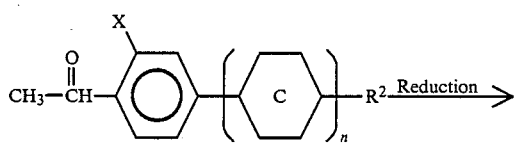

wherein X, n,

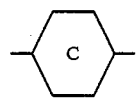

and $R^2$ are as defined in the above formula (I).

The optical resolution through ester exchange reaction is suitably carried out by subjecting a racemic alcohol together with a triglyceride such as tributyrin to the reaction substantially in the absence of moisture, for example by the addition of an enzyme such as lipase in a liquid phase at 20° to 100° C. As the enzyme, commercially available products may be used.

The reaction time is in the range of one to several tens days. After the reaction, the enzyme is filtered off, followed by isolating the resulting alcohol from unreacted alcohol by separation means such as distillation, chromatography, etc. The isolated alcohol is one of a pair of antipodes and the other optically active alcohol is obtained by hydrolyzing the formed ester.

The thus obtained optically active compound of the above-mentioned formula (II) is a novel compound constituting the fundamental skeleton of the compound of the above-mentioned formula (I).

A first specific feature of the compound of the present invention consists in that when the compound is used as a dopant for liquid crystal compositions, its addition in a slight quantity induces a highly twisted structure.

As shown in Example 4 mentioned later, when the compound is added in 1% by weight to a liquid crystal composition having no twist structure, the resulting pitch is as short as 7.4 μm at 25° C., and by its addition in a less quantity, it is possible to prepare a liquid crystal composition having an optimized twist structure i.e. a chiral liquid crystal composition.

The above specific feature is surprising enough, taking into account the fact that an optically active compound currently known as a dopant, for example, C-15 (tradename of a product made by BDH Company) has a pitch of 63 μm, and even CB-15 (tradename of a product made by the same company) has nothing but 10 μm.

Further, a second specific feature of the compound of the present invention consists in that it has a negative temperature characteristic. As shown in Example 4, the temperature characteristic δP is −0.189 at $t_1=20°$ C. versus $t_2=40°$ C., that is, the compound exhibits a negative temperature characteristic.

Thus, when the compound is mixed in a suitable quantity with compounds optionally selected from a group of compounds generally known to have a positive temperature characteristic, it is possible to readily provide a chiral composition having a flat temperature characteristic of pitch, that is, δP=0.

A number of these superior characteristics of the compound of the present invention are all originated from the core thereof

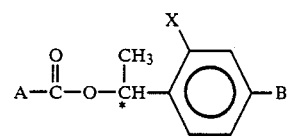

and without this core, the above-mentioned characteristics cannot be exhibited. In other words, only if the above-mentioned core is contained in a molecular structure, the superior characteristics can be exhibited, and it goes without saying that it is possible to replace various structures at the parts of A and B.

Namely, when two kinds optionally chosen from among various kinds of carboxylic acids and various optically active alcohols both shown below are combined, it is possible to obtain compounds having similar performance to those of compounds shown in Examples.

Carboxylic acids

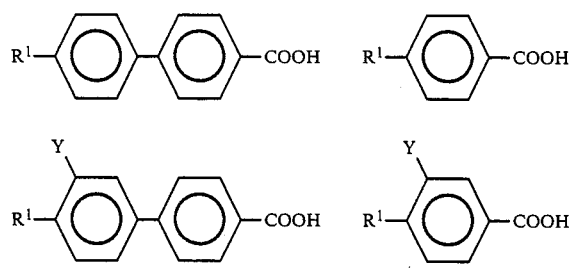

-continued
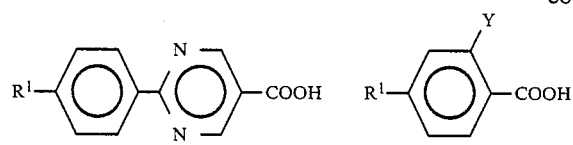
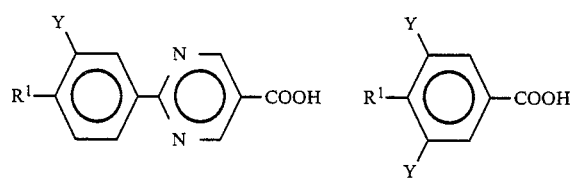
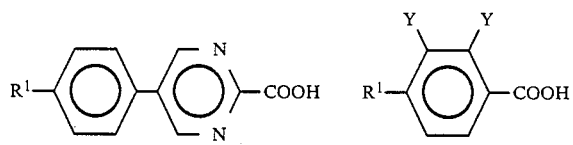
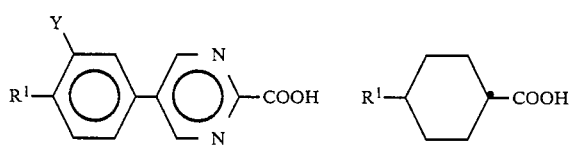
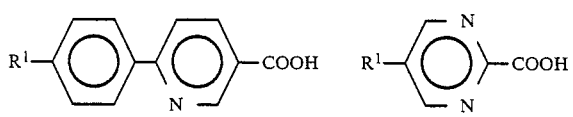
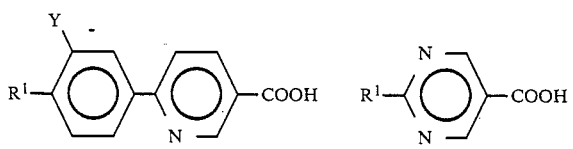
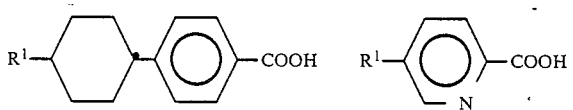
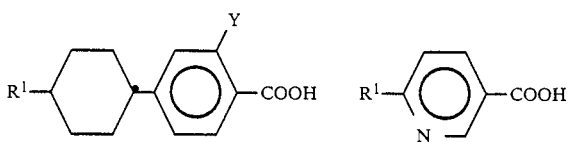
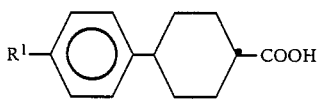
Optically acitve alcohols
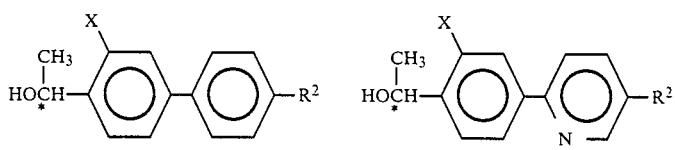

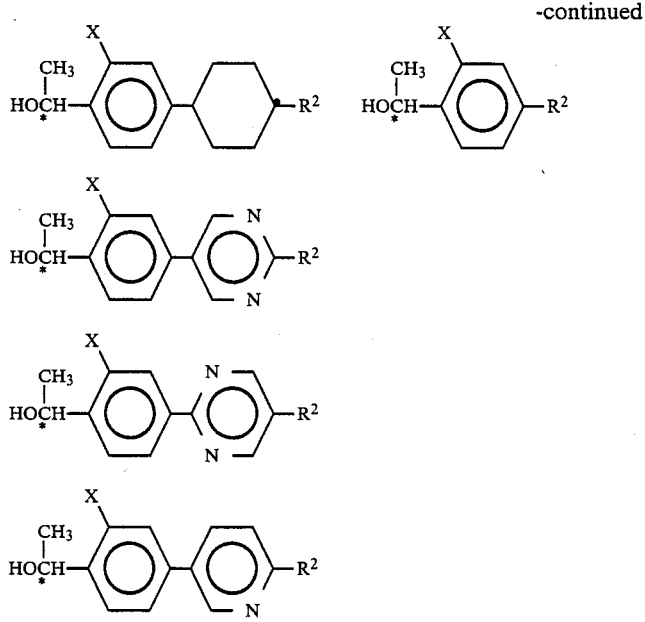

Further, since the compound of the present invention has a high twistability, the quantity of the compound added necessary for obtaining a chiral liquid crystal composition having an optimized twisted structure may be sufficient to be slight. Thus, it is possible to blend the compound with various kinds of liquid crystal substances. Examples of such various liquid crystal substances are Schiff's bases, biphenyls, phenylcyclohexanes, phenylpyridines, phenylpyrimidines, phenyldioxanes, cyclohexylbiphenyls, cinnamic acid esters, phenyl esters, liquid crystal compositions obtained by optionally choosing substances from among the foregoing compounds and combining these substances, etc.

Further, the chiral liquid crystal composition obtained by adding the compound of the present invention, referred to herein, i.e. a liquid crystal composition having a twisted structure, is not limited only to chiral nematic compositions, but it also means compositions having a twisted structure exhibited within smectic phases, particularly smectic C phase. In recent years, research on a novel driving mode utilizing chiral smetic C phase has been extensively made (Clark et al.; Applied Phys. lett., 36, 899 (1980)), and when the compound of the present invention is added to a compound or composition having smectic C phase, it is possible to obtain a chiral smectic composition.

The preparation of the compound of the present invention and superior characteristics thereof will be described in more detail by way of Examples.

EXAMPLE 1

Preparation of optically active 1-(2-bromophenyl)ethanol

An enzyme (Amano CES, tradename of a lipase made by Amano Seiyaku Company) (10 g), ±-1-(2-bromophenyl)ethanol (7.0 g, 35 mmol) and tributyrin (15.9 g, 52.5 mmol) were placed in a three-necked flask, followed by agitating these materials at 35° C. for 15 days, stopping the reaction, thereafter filtering off the enzyme, concentrating the filtrate and subjecting the concentrate to silica gel chromatography to isolate the respective objective products. As a result, (S)-1-(2-bromophenyl)ethanol ($[\alpha]_D^{23.5°}$ $^C$: $-26.3°$ (C 3.72, CHCl$_3$)) (2.6g) and R-1-(2-bromophenyl)-1'-butanoyloxyethane (25 g) were obtained, followed by hydrolyzing the latter compound to obtain R-1-(2-bromophenyl)ethanol ($[\alpha]_D^{23.5°}$: 30 33.5° (C 3.52, CHCl$_3$)) (1.7 g).

Further, the above-mentioned compounds were analyzed according to liquid chromatography using an optical resolution column (CHIRAL CELL OB, trademark of device made by Daicel Kagaku Kogyo Company. As a result, the compounds had the following optical purities:

S-1-(2-bromophenyl ethanol: 68% ee
R-1-(2-bromophenyl)ethanol: 95% ee

EXAMPLE 2

Preparation of R-4-pentyloxybiphenyl-4'-carboxylic acid 1-(2-bromophenyl)ethyl ester (a compound of the formula (I) wherein l=m=1; n=0; R$^1$=C$_5$H$_{11}$O—; R$^2$=H; X=Br; and

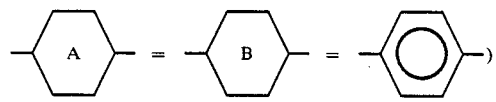

A mixture of R-1-(2-bromophenyl)ethanol ($[\alpha]_D^{23.5}$: +33.5 (C=3.52, CHCH$_3$)) (4 g), 4-pentyloxybiphenyl-4'-carboxylic acid (6 g), dicyclohexylcarbodiimide (7 g), dimethylaminopyridine (0.4 g) and dichloromethane (100 ml) was agitated at room temperature for 2 hours, followed by filtering off insolubles, washing the filtrate with an acid, then with an alkali and further with water, distilling off the solvent and recrystallizing the residue from a mixed solvent of ethanrol with ethyl acetate to obtain R-4-pentyloxybiphenyl-4'-carboxylic acid 1-(2-bromophenyl)ethyl ester (7.6 g). M.P.: 101.2°–102.2° C. According to the elemental analysis, NMR-spectra and IR-spectra of this product, the product accorded with the captioned compound.

The values of the elementary analysis of the product were as follows:

|   | Observed value | Theoretical value (in terms of $C_{26}H_{27}O_3Br$) |
|---|---|---|
| C | 66.90 | 66.81 |
| H | 5.80 | 5.82 |
| Br | 17.20 | 17.10 |

EXAMPLE 3

Preparation of R-4-pentyloxybiphenyl-4'-carboxylic acid 1-(2-cyanophenyl)ethyl ester (a compound of the formula (I) wherein $l=m=1$; $n=0$; $R^1=C_5H_{11}O-$; $R^2=H$; $X=CN$; and

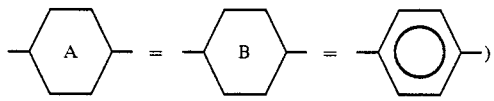

)

A mixture of R-4-pentyloxybiphenyl-4'-carboxylic acid 1-(2-bromophenyl)ethyl ester (6 g) prepared in Example 2, cuprous cyanide (2.1 g) and dimethylformamide (40 ml) was agitated at 150° C. for 6 hours, followed by cooling the resulting material, adding a mixture of ferrous chloride (6.4 g) with 20% hydrochloric acid (7 ml), agitating the resulting mixture at 60°–70° C. for 20 minutes, adding toluene, washing the mixture with water, distilling off the solvent and recrystallizing the residue from ethanol to obtain R-4-pentyloxybiphenyl-4'-carboxylic acid 1-(2-cyanophenyl)ethyl ester (2.8 g). M.P.: 112.5°–112.8° C. According to the elemental analysis, NMR-spectra and IR-spectra of this product, the product accorded with the captioned compound.

The values of the elementary analysis of the product were as follows:

|   | Observed value | Theoretical value (in terms of $C_{27}H_{27}O_3N$) |
|---|---|---|
| C | 78.40% | 78.42% |
| H | 6.60% | 6.58% |
| N | 3.40% | 3.39% |

EXAMPLE 4

(Use example 1)

To a nematic liquid crystal composition (ZLI-1132, tradename of a commercially available product made by Merck Company) were added the following compounds of Example 2 and Example 3 each in 1% by weight:

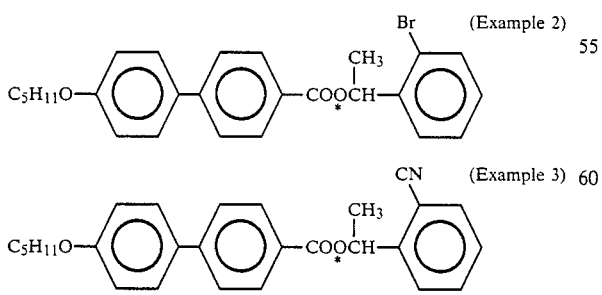

to prepare a chiral nematic liquid crystal composition. This composition was then filled in a wedge type cell subjected to parallel treatment and observed under a polarizing microscope. As a result, helical pitches as shown in the following Table were observed:

TABLE

|   | Temperature (°C.) | | | | | | |
|---|---|---|---|---|---|---|---|
|   | 20 | 25 | 30 | 40 | 50 | 60 | 70 |
| Example 2 | | | | | | | |
| Pitch length (μm) | 9.8 | 9.7 | 9.6 | 9.5 | 9.5 | 9.5 | 9.5 |
| $\delta P_{20\sim T}$ | X | X | −0.190 | −0.144 | −0.096 | −0.072 | −0.052 |
| Example 3 | | | | | | | |
| Pitch length (μm) | 7.5 | 7.4 | 7.3 | 7.2 | 7.1 | 7.0 | |
| $\delta P_{20\sim T}$ | X | X | −0.250 | −0.189 | −0.169 | −0.159 | |

The above-mentioned $\delta P_{20\sim T}$ refers to a parameter expressing a temperature characteristic and is defined by the following equation:

$$\delta Pt_1 \sim t_2 = \frac{2(P(t_1) - P(t_2))}{P(t_1) + P(t_2)} \times \frac{100}{t_1 - t_2}$$

wherein P(t): pitch length at t° C., t: temperature.

As described above, the composition has a characteristic that the exhibited pitch is very short and moreover the pitch length becomes shorter with temperature rise; hence it is seen that the compound of the present invention is a superior agent for adjusting the pitch of liquid crystal compositions.

EXAMPLE 5

(Use example 2)

The compound of Example 2 (20% by weight) was added to a racemic compound having the following formula and having the following phase transition points (80% by weight):

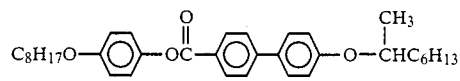

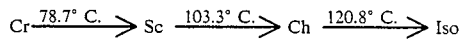

to prepare a chiral smectic C liquid crystal composition. Its phase transition points were as follows:

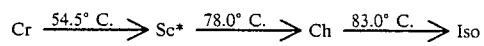

The spontaneous polarization value of this composition was measured to give 10.4 nC/cm$^2$.

What we claim is:

1. An optically active compound expressed by the formula

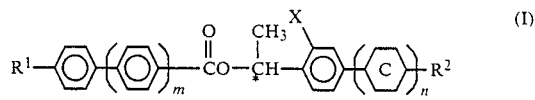

(I)

wherein $R^1$ and $R^2$ each represent an alkyl group or an alkoxy group each of 1 to 20 carbon atoms or hydrogen atom, m and n each represents 1 or either one thereof represents zero, n represents 1 or 0, X represent fluorine atom, chlorine atom, bromine atom or cyano group and represents 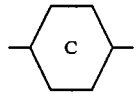
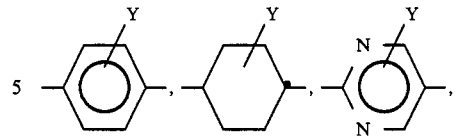
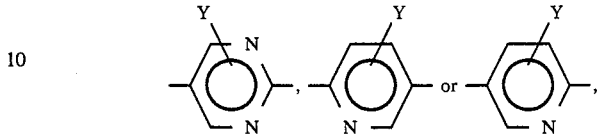
wherein Y represent either one of hydrogen atom, halogen atom or cyano group.
2. A liquid crystal composition comprising at least two components, at least one of which is an optically active compound as set forth in claim 1.
* * * * *